United States Patent [19]

Tanaka et al.

[11] 4,225,634

[45] Sep. 30, 1980

[54] METHOD FOR MANUFACTURING GAS COMPOSITION DETECTOR

[75] Inventors: Kazuo Tanaka, Toyoake; Osamu Takenaka, Chiryu; Masatosi Suzuki, Kariya, all of Japan

[73] Assignee: Nippondenso Co., Ltd., Aichi, Japan

[21] Appl. No.: 817,523

[22] Filed: Jul. 20, 1977

[30] Foreign Application Priority Data

Jul. 28, 1976 [JP] Japan .................................. 51-90462

[51] Int. Cl.$^2$ .......................... F01N 3/00; B01J 35/04
[52] U.S. Cl. ................................ 427/101; 204/195 S; 427/125; 427/245; 427/304; 427/380; 427/383.5; 427/426
[58] Field of Search .................... 204/195 S; 427/125, 427/380, 383, 245, 426, 101, 304

[56] References Cited

U.S. PATENT DOCUMENTS

| | | |
|---|---|---|
| 2,950,996 | 8/1960 | Place, Sr. et al. |
| 3,630,768 | 12/1971 | Bianchi .............................. 427/12 S |
| 3,653,946 | 4/1972 | Fefferman .......................... 427/125 |
| 3,841,987 | 10/1974 | Friese et al. ...................... 204/195 S |
| 3,843,400 | 10/1974 | Radford ............................ 204/195 S |
| 3,935,089 | 1/1976 | Togawa ............................ 204/195 S |
| 3,978,006 | 8/1976 | Topp ................................. 204/195 S |
| 3,983,266 | 9/1976 | Bahls ................................ 427/426 |
| 4,080,276 | 3/1978 | Bode ................................ 204/195 S |

Primary Examiner—John D. Smith
Attorney, Agent, or Firm—Cushman, Darby & Cushman

[57] ABSTRACT

A gas composition detector, particularly an oxygen concentration detector includes a metal oxide an electrical resistance or an electromotive force of which is changed by oxygen ions which are conducted in accordance with a difference between an oxygen concentration of gas being examined and an oxygen concentration of a reference gas. A surface of the metal oxide is coated with a conductive metal electrode, and a metal which is the same as or different than the conductive metal penetrates into the metal oxide at the interface of the metal oxide and the conductive metal, whereby the tear-off of the electrode is prevented.

6 Claims, 6 Drawing Figures

METHOD FOR MANUFACTURING GAS COMPOSITION DETECTOR

BACKGROUND OF THE INVENTION

1. Field of the Invention

The present invention relates to a gas composition detector, and more particularly to an oxygen concentration detector for detecting oxygen concentration in exhaust gas of a motor vehicle and a method for manufacturing the same. More specifically, the present invention intends to prevent tear-off of an electrode.

2. Description of the Prior Art

A prior art oxygen concentration detector includes an oxygen concentration detection element made of an oxygen ion conductive metal oxide, and conductive metal layers such as platinum (Pt) layers are formed as electrodes on the sides of the oxygen concentration detection element facing the gas to be examined and reference gas, respectively.

However, since the electrode facing the gas to be examined is exposed to the gas, it is torn off during the use over a long period where a flow rate or temperature of the gas to be examined such as exhaust gas of a motor vehicle changes materially, so that the detector can no longer operate. The causes of this problem lie in that the oxygen concentration detection element is made of a metal oxide while the electrodes coated thereon are made of a metal and they are incompatible with each other, and that the electrodes are merely deposited on the surfaces of the oxygen concentration detection element and hence the disposition strength is weak.

SUMMARY OF THE INVENTION

It is an object of the present invention to provide a gas composition detector, particularly an oxygen concentration detector which is free from the drawbacks encountered in the prior art detector and which prevents the tear-off of the electrodes during the use over a long period.

According to the present invention, a conductive metal film is formed on that surface of the oxygen concentration detection element which is exposed to the gas to be examined such that the conductive metal film penetrates into said surface, and an electrode made of a conductive metal is formed on the surface of the conductive metal film. Thus, the conductive metal film on the surface of the oxygen concentration detection element penetrates into the surface of the oxygen concentration detection element and it is strongly bonded to the oxygen concentration detection element. Further, since the electrode formed on the surface of the conductive metal film is made of the conductive metal, they are both metals and hence compatible with each other. Therefore, the deposition strength therebetween is high and the electrode will not be torn off after long term use. Accordingly, a highly durable oxygen concentration detector can be provided.

DESCRIPTION OF THE PREFERRED EMBODIMENT

In the present invention, there are many ways to form the conductive metal film on the surface of the oxygen concentration detection element such that it penetrates into the surface. One example thereof is at first explained below with reference to FIG. 4.

Figure 3:
FIG. 3 is an organization chart showing the formation of a Pt-film on a surface of an oxygen concentration detection element.
Figure 4:
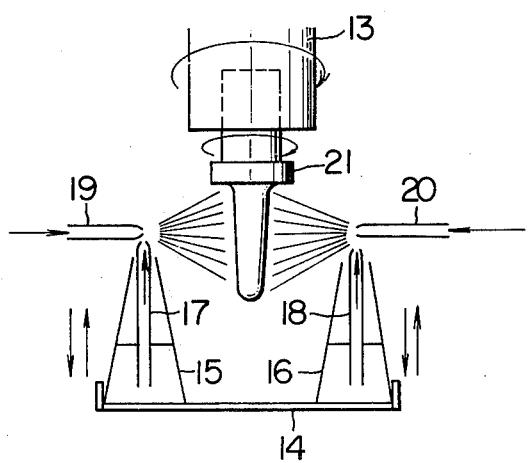
FIG. 4 shows an apparatus used in one method for forming the Pt-film on the surface of the oxygen concentration detection element.

By way of example, 85 mole % of zirconium oxide ($ZrO_2$) and 15 mole % of calcium oxide are mixed together and broken to pieces. The mixture is provisionally calcined at 1300° C. to 1400° C. for about 10 hours and then shaped into a desired shape to form a pre-calcined mold. The resulting mold 21 is mounted on a rotor 13 of a device for manufacturing the gas composition detector as shown in FIG. 4. On the other hand, a container 15 containing a solution of chloroplatinic acid at a concentration of 5 g/l (ratio for one liter of water) and a container 16 containing a solution of sodium borohydrate ($NaBH_4$) at a concentration of 4 g/l (ratio for one liter of water) are mounted on a platform 14, and glass tubes 17 and 18 are inserted in the containers 15 and 16, respectively. The mold 21 is rotated by the rotor 13 while the platform 14 is moved vertically as indicated by arrows. At the same time, air is supplied through metal tubes 19 and 20 to spray the $H_2PtCl_6$ solution and the $NaBH_4$ solution simultaneously to the surface of the rotating mold 21 to cause a reducing reaction to occur on the surface of the mold 21 to deposit Pt on the surface of the mold 21. In this case, the rate of the spray amount by weight of the $H_2PtCl_2$ solution to that of the $NaBH_4$ solution may be 1, for example. The spray process may be carried out in an atmospheric environment and a spray time of 5 to 15 seconds may be appropriate. Since the surface of the pre-calcined mold 21 is porous, the Pt particles not only deposit on the surface of the mold but also penetrate continuously into the inside thereof. The Pt particles on the surface are contiguous with penetrated Pt particles. After the deposition of Pt on the surface of the mold in the manner described above, the mold is dried at 80° C. to 100° C. for about 0.5 to 1.0 hour, and then the mold is fired at 1600° C. to 1700° C. for about 2 hours. Through this firing process, the mold is formed into a solid sintered body of the metal oxides. By contraction of the mold during the firing process, the Pt particles deposited on the surface of the mold and Pt particles penetrate into the inside thereof during the calcining process of the mold and are strongly held to the sintered body so that a Pt film which penetrates into the inside of the sintered body and hence is strongly bonded thereto is formed on the surface of the sintered body. This sintered body forms the oxygen concentration detection element to be described later. FIG. 3 shows an enlarged view illustrating the formation of the Pt film on the surface of the sintered body. In FIG. 3, numeral 1 denotes the sintered body of the metal oxides and 2a denotes the Pt particles penetrating into the sintered body 1 forming the Pt film 2.

Figure 1:
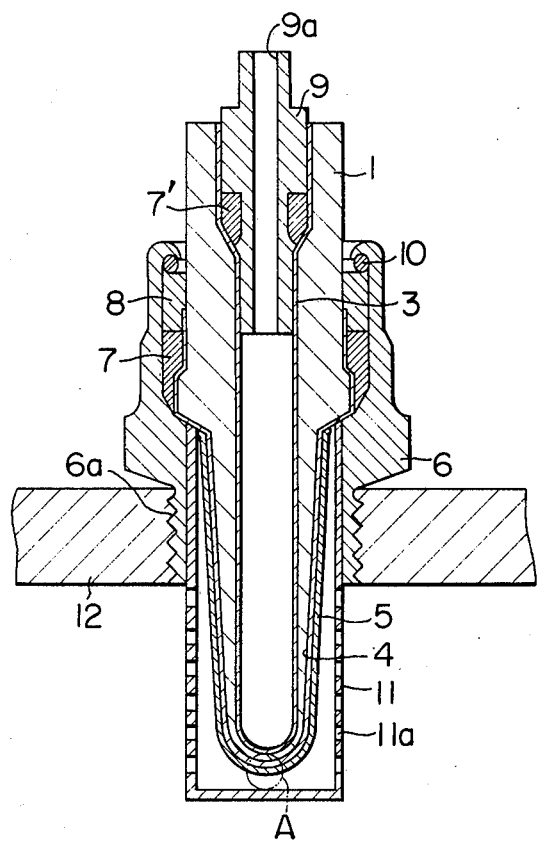
FIG. 1 is a sectional view illustrating one embodiment of a detector of the present invention.
Figure 2:
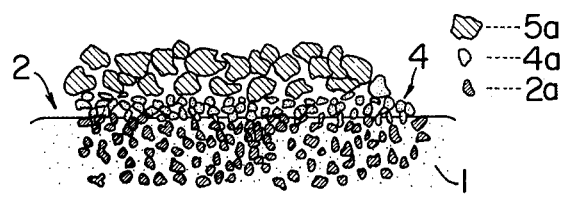
FIG. 2 is an organization chart showing a portion A in FIG. 1 in an enlarged scale.

A structure of one embodiment of the detector of the present invention is now explained with reference to FIG. 1. In FIG. 1, numeral 1 denotes the oxygen concentration detecting element made of the sintered body of an oxygen ion conductive metal oxide such as zirconium oxide, calcium oxide or the like. In the present embodiment, it is a solid sintered body made of a solid solution of 85 mole % of $ZrO_2$ and 15 mole % of CaO as explained above. The oxygen concentration detection element 1 is of a cup shape and as is well-known it has a property of conducting oxygen ions at a temperature suited to conduct the oxygen ions, e.g. at 300° C. to 1000° C. when there exists a difference in the oxygen concentration across the oxygen concentration detection element 1. As shown in FIG. 2, there is formed a Pt film on the outer surface of the oxygen concentration detection element 1 which Pt film penetrates into the outer surface to the depth of approximately 0.1 mm and hence is strongly bonded to the oxygen concentration detection element 1. The method for forming the Pt film has been described above. The Pt particles forming the Pt film 2 are of approximately $0.2\mu$ in size and thickness of the film is approximately $0.5\mu$. Formed on an inner peripheral surface of the oxygen concentration detection element 1 which is not exposed to the gas is a thin layer electrode 3 made of catalytic conductive metal such as a Pt layer having a particle size of approximately $0.2\mu$, by chemical plating or paste baking. The thickness of the electrode 3 is approximately $1\mu$. Formed on the surface of the Pt film 2 on the outer surface of the oxygen concentration detection element 1 is a thin layer electrode 4 made of a catalytic conductive metal such as Pt having a particle size of approximately $0.2\mu$ and having a thickness of approximately $1\mu$. The electrode 4 may be formed by chemical plating or paste baking of fine Pt particles. The Pt particles forming the Pt film 2 and the Pt particles forming the electrode 4 are deposited contiguous with each other as shown in FIG. 2. Since the Pt film 2 and the electrode 4 are formed by the same kind of Pt particles, the Pt film 2 and the electrode 4 are strongly bonded to each other. In FIG. 2, numeral 1 denotes the oxygen concentration detection element, 2a denotes the Pt particles forming the Pt film 2, and 4a denotes the Pt particles of the electrode 4. In FIG. 1, numeral 5 denotes a porous, heat resistive coating formed on the surface of the electrode 4. The coating 5 may be a metal oxide such as $Al_2O_3$, $ZrO_2$, MgO or a compound metal oxide such as $Al_2O_3$—$SiO_2$, $MgO.Al_2O_3$, $MgO.ZrO_2$. The particles of the coating 5 are designated by 5a in FIG. 2. Numeral 6 denotes a housing made of a heat resistive and electrically conductive metal. It is of a cylindrical shape and has a thread 6a at the bottom thereof for screw-mounting the housing to an exhaust pipe 12. The oxygen concentration detection element 1 is mounted within the housing 6. At the top of the housing 6, a graphite ring 7 and an O-ring 8 are inserted in a space between the housing 6 and the oxygen concentration detection element 1 and a pressure of 500 kg/cm$^3$, for example, is applied to the O-ring 8 from the top thereof to fix the oxygen concentration detection element 1. Numeral 9 denotes a stem made of a conductive metal and it is fixed within the oxygen concentration detection element 1 by a conductive graphite ring 7' by applying a pressure of 150 kg/cm$^2$, for example. An access hole 9a is formed in the stem 9 so that the inside of the oxygen concentration detection element 1 is exposed to the atmosphere. A caulking ring 10 is disposed on the O-ring 8 and the upper edge of the housing 6 is inwardly caulked at that portion by cold calking or the like so that the oxygen concentration detection element 1 is strongly fixed to the housing 6. The housing 6 is electrically connected to the electrode 4 through the conductive graphite ring 7 and the stem 9 is electrically connected to the electrode 3 through the conductive graphite 7'. Accordingly, an electromotive force generated by the oxygen concentration detection element 1 is taken out across the housing 6 and the stem 9. Numeral 11 denotes a protective tube having a number of apertures 11a.

The operation of the construction described above is now explained. The oxygen concentration detector is screwed to the exhaust pipe 12 of an internal combustion engine through the housing 6 so that the oxygen concentration detection element 1 is exposed to the exhaust gas. As is well known, the exhaust gas consists of gas ingredientes such as $O_2$, CO and HC, and the concentrations of the respective ingredients change depending on an air-fuel ratio of air-fuel mixture prior to combustion. The oxygen concentration detection element 1 produces an electromotive force corresponding to a difference between an oxygen concentration in the exhaust gas on the side of the electrode 4 and an oxygen concentration in a reference atmosphere on the side of the electrode 3. By the catalytic action of the Pt film 2 and the electrode 4 of the oxygen concentration detection element 1 which are exposed to the exhaust gas, the $O_2$ in the gas contributes to the oxidization of CO and HC on the surface of the oxygen concentration detection element 1 which is exposed to the exhaust gas. It is thus seen that the oxygen concentration in the gas on the surface of the oxygen concentration detection element 1 which is exposed to the exhaust gas is low when the air-fuel ratio is lower (richer) than a stoichiometric air-fuel ratio, and the oxygen concentration in the gas is high when the air-fuel ratio is higher (leaner) than the stoichiometric air-fuel ratio. As a result, the electromotive force generated by the oxygen concentration detection element 1 changes abruptly around the stoichiometric air-fuel ratio. When an electromotive force corresponding to the stoichiometric air-fuel ratio is used as a reference voltage, it can be determined that the detected air-fuel ratio is lower than the stoichiometric air-fuel ratio if the electromotive force corresponding to the detected air-fuel ratio, when compared with the reference voltage, is higher than the reference voltage. Conversely, it can be determined that the detected air-fuel ratio is higher than the stoichiometric air-fuel ratio if the electromotive force is lower than the reference voltage. Thus, the system can be controlled such that the air-fuel ratio coincides with the stoichiometric air-fuel ratio. As is well known, it is near the stoichiometric air-fuel ratio that the three gas ingredients, CO, HC and $NO_x$ of the exhaust gas are minimum. Accordingly, in a motor vehicle having a catalytic device for cleaning those three gas ingredients simultaneously, the control of the air-fuel ratio to the stoichiometric air-fuel ratio leads to the maximum attainment of the cleaning function of the catalytic device.

As is well known, the temperature and the flow rate of the exhaust gas change so materially that the electrodes in the prior art detector have been torn off after long term usage. In the present embodiment, since the Pt film 2 is formed on the outer surface of the oxygen concentration detection element 1 which is exposed to the exhaust gas such that the Pt film 2 penetrates into the outer surface and the electrode 4 is formed on the surface of the Pt film 2, the Pt film 2 penetrates into the inside of the oxygen concentration detection element 1 and hence it is strongly bonded to the outer surface of the oxygen concentration detection element 1. Furthermore, since both the electrode 4 and the Pt film 2 are made of Pt metal, the deposition strength therebetween is strong and the electrode 4 remains strongly bonded to the outer surface of the oxygen concentration detection element 1 and it is not readily torn off. Furthermore, in the present embodiment, since the porous coating 5 through which the exhaust gas can pass is formed on the surface of the electrode 4, lead compound, phosphorous compound and the like in the exhaust gas do not directly deposit on the electrode 4 but deposit on the coating 5 so that the deterioration of the catalytic action of the electrode 4 is prevented. In other words, the coating 5 serves as a filter.

Now, comparison between the performance of te oxygen concentration detector of the present invention with that of a prior art oxygen concentration detector is made. Two oxygen concentration detector is made. Two oxygen concentration detectors were prepared for the test. Sample 1 of the detectors had the same construction according to the invention as shown in FIG. 1 and sample 2 had a similar construction as that of FIG. 1 according to the prior art detector except that the electrode was formed directly on the surface of the oxygen concentration detection element which was exposed to the exhaust gas without forming the Pt film 2 shown in FIG. 1. The sample 1 and sample 2 detectors were tested for initial electromotive force characteristic curve under the test condition shown below, and then subjected to durability test under the durability condition shown below and then tested for the electromotive force characteristic curve after the durability test under the same test condition.

(1) Test condition:
 Internal combustion engine under test
  6 cylinders, 2000 cc (with carburetor)
 Rotation speed of internal combustion engine
  1600 r.p.m.
 Suction manifold pressure
  500 Torr
 Exhaust gas temperature
  570° C.
 Fuel used—Lead free gasoline
(2) Durability condition:
 The outer surfaces of the sample 1 and sample 2 oxygen concentration detection elements were exposed to combustion flame (at 900° C.) for 300 hours, using a city gas burner.

Figure 5:
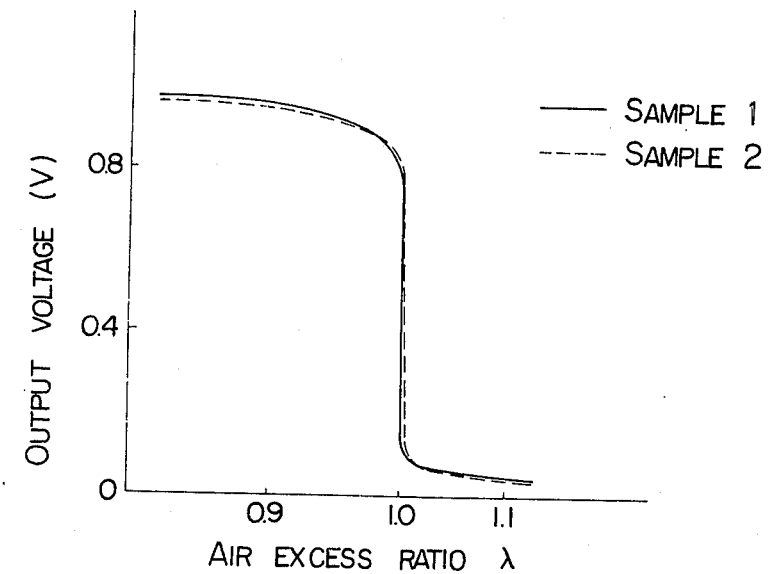
FIG. 5 shows a characteristic chart prior to a durability test for illustrating an effect of the detector of the present invention.
Figure 6:
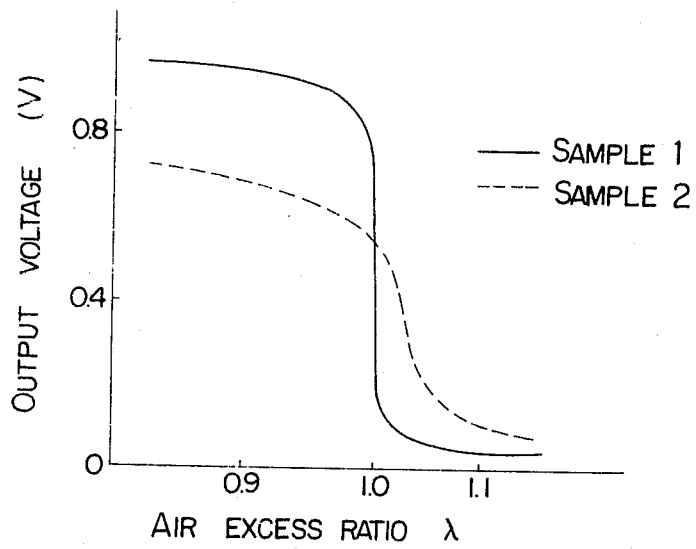
FIG. 6 shows a characteristic chart after the durability test for illustrating the effect of the detector of the present invention.

The results of the test are shown in FIGS. 5 and 6. In FIG. 5 which shows the initial electromotive force characteristic curves prior to the durability test, the sample 1 and the sample 2 exhibit substantially the same characteristic. On the other hand, in FIG. 6 which shows the result after the durability test, the sample 1 exhibits the substantially same characteristic as the electromotive force curve prior to the durability test while the sample 2 exhibits an electromotive force characteristic curve which is considerably shifted from that prior to the durability test. By way of example, visual observation of the electrode of the sample 1 after the durability test showed no tear-off while the visual observation of the electrode of the sample 2 after the durability test showed the tear-off everywhere. This caused the substantial shift of the electromotive force characteristic curve.

It is seen from FIGS. 5 and 6 that the detector of the present invention has a very excellent durability.

In the above embodiment, while the size of the Pt particles forming the Pt film 2 and the electrodes 3 and 4 is not defined, the size of the Pt particles should be determined such that the oxygen ions can fully conduct.

Furthermore, while the Pt is used as the conductive metal forming the film 2 and the electrodes 3 and 4 in the above embodiment, other catalytic metal such as Pd, Au, Ru or Ag or an alloy thereof may be used, and even a combination such as Pd for the film 2 and Pt for the electrodes 3 and 4 may, for example, be used. The material of the film 2 need not be limited to the catalytic conductive metal but it may be Ni or Cu. The same is true for the electrodes 3 and 4.

Further, although the oxygen concentration detection element 1 is of the cup shape having one open end and the other end closed in the above embodiment, it may be of a plate shape or cylindrical shape.

Moreover, the present invention is not limited to means for detecting oxygen concentration in the exhaust gas exhausted from the internal combustion engine to detect the air-fuel ratio of the air-fuel mixture supplied to the internal combustion engine as shown in the above embodiment, but it may be used as means for detecting oxygen concentration in the combustion product exhausted from a combustion apparatus such as a blast furnace or boiler to detect the air-fuel ratio of an air-fuel mixture supplied to the combustion apparatus (in order to improve a heat efficiency of the combustion apparatus, for example).

The experiment by the inventors proved that when the oxygen concentration detection element 1 was made of an oxygen ion conductive metal oxide consisting of solid solution of 90–92 mole % of $ZrO_2$ and 10–8 mole % of $Y_2O_3$, the conductivity was improved and the oxygen ions could be conducted even at a low temperature.

The solid solution composition of the sintered body forming the oxygen concentration detection element 1 is not limited to $ZrO_2$-$CaO$ as shown in the above embodiment but it may be a solid solution composition of 70–95 mole % of tetra-valent metal oxide such as $TnO_2$ or $CeO_2$ and 30–5 mole % of divalent or trivalent metal oxide such as $CaO$, $Y_2O_3$ or $MgO$.

Furthermore, the experiment by the inventors proved that when the film 2 formed on the outer surface of the oxygen concentration detection element 1 had a conductivity, the film 2 itself could constitute the electrode. In order to impart the conductivity to the film 2, it is necessary to increase the deposition density of the particles forming the film 2 to the oxygen concentration detection element 1. Particularly, in the process of forming the film 2 shown in FIG. 4, the spray time for the $H_2PtCl_6$ solution and the $NaBH_4$ solution may be extended.

What is claimed is:
1. A method for manufacturing a gas composition detector comprising a metal oxide mixture, the electrical resistance or the electromotive force of which changes with the concentration of the gas composition of gas to be examined, said method comprising the steps of:
 pre-calcining said metal oxide mixture to form a preform detection element having a porous surface of sufficient porosity to permit a aqueous solution including a conductive metal component to penetrate said pre-calcined detection element;

spraying said aqueous solution including said conductive metal component on said pre-calcined element;

drying said pre-calcined detection element;

firing said detection element to cause further sintering of said element whereby said porous surface is concentrated and some particles of said conductive metal component penetrate the concentrated porous surface of said detection element while other particles remain on said surface, to cause the penetrated particles and the other particles of said conductive metal component to be strongly deposited on the porous surface; and forming an electrode layer of the same metal as said conductive metal component on a surface of the fired detection element through said conductive metal component, the metal protrusions on the surface of the detection element from said strongly deposited conductive metal component serving as a base for the metal plating in said forming step to provide strong adhesion between the metal layers in the first and second metal deposition steps.

2. A method for manufacturing a gas composition detector according to claim 1, wherein said calcining step includes calcining the detection element consisting of 85 mole % of zirconium oxide and 15 mole % of calcium oxide at 1300° C. to 1400° C. for about 10 hours.

3. A method for manufacturing a gas composition detector according to claim 2, wherein said spraying step of said aqueous solution includes spraying a solution of chloroplatinic acid at a concentration of 5 g/1 and a solution of sodium hydroborate at the concentration of 4 g/l simultaneously on a surface of the calcined detection element for 5 to 15 seconds.

4. A method for manufacturing a gas composition detector according to claim 3, wherein the ratio of the spray amount by weight of said chloroplatinic acid to that of said sodium borohydrate is 1.

5. A method for manufacturing a gas composition detector according to claim 3, wherein said drying step is carried out at 80° C. to 100° C. for about 0.5 to 1 hour.

6. A method for manufacturing a gas composition detector according to claim 5, wherein said firing step is carried out at 1600° C. to 1700° C. for about 2 hours.

* * * * *